United States Patent
Metcalfe

(10) Patent No.: US 6,841,373 B2
(45) Date of Patent: Jan. 11, 2005

(54) HERPES VIRUS COMPLEMENTING CELL LINE

(75) Inventor: Karen Metcalfe, Wilmington, MA (US)

(73) Assignee: AVANT Immunotherapeutics, Inc., Needham, MA (US)

(*) Notice: Subject to any disclaimer, the term of this patent is extended or adjusted under 35 U.S.C. 154(b) by 12 days.

(21) Appl. No.: 10/257,229

(22) PCT Filed: Apr. 10, 2001

(86) PCT No.: PCT/US01/11775

§ 371 (c)(1), (2), (4) Date: Oct. 10, 2002

(87) PCT Pub. No.: WO01/78776

PCT Pub. Date: Oct. 25, 2001

(65) Prior Publication Data

US 2003/0049830 A1 Mar. 13, 2003

Related U.S. Application Data

(60) Provisional application No. 60/196,801, filed on Apr. 13, 2000.

(51) Int. Cl.$^7$ .............................. C12N 5/10; C12N 7/04
(52) U.S. Cl. ................ 435/235.1; 435/236; 435/325; 435/364; 424/205.1; 424/231.1; 424/93.2
(58) Field of Search ...................... 424/231.1, 205.1, 424/93.2; 435/173.3, 235.1, 325, 236, 364

(56) References Cited

U.S. PATENT DOCUMENTS 5,658,724 A * 8/1997 DeLuca ........................ 435/5
5,972,666 A 10/1999 Hippenmeyer et al.

OTHER PUBLICATIONS

Berstein and Stanberry, *Vaccine*, 17: 1681–1689 (1999).
Bourne et al., *Antiviral Res.*, 40(3): 139–144 (1999).
Boursnell et al., *J. Infect. Dis.*, 175: 16–25 (1997).
Cadoz et al., *Lancet*, 339: 1429–1432 (1992).
Curtiss et al., *Dev. Bio. Stand.*, 82: 23–33 (1994).
Da Costa et al., *Virology*, 232: 1–12 (1997).
Farrell et al., *J. Virol.*, 68: 927–932 (1994).
Krause and Straus, *Infect. Dis. Clin. North Am.*, 13: 61–81 (1999).
McLean et al., *J. Infect. Dis.*, 170: 1100–1109 (1994).
McLean et al., *Vaccine*, 14: 987–992 (1996).
Morrison and Knipe, *J. Virol.*, 68: 689–696 (1994).
Morrison et al., *Virology*, 243: 178–187 (1998).
Nguyen et al., *J. Virol.*, 66: 7067–7072 (1992).
Stanberry, *Sexually Transmitted Infect.*, 74(6): 391–394 (1998).
Straus et al., *J. Infect. Dis.*, 176: 1129–1134 (1997).

* cited by examiner

*Primary Examiner*—Laurie Scheiner
(74) *Attorney, Agent, or Firm*—Leon R. Yankwich; Yankwich & Associates

(57) ABSTRACT

The present invention is directed to a cell line capable of supporting replication of a growth-defective Herpes Simplex Virus strain; specifically a replication-defective HSV-2 double mutant. Particularly disclosed is a cell line that expresses the ICP8 protein and the UL5 protein of Herpes Simplex Virus. This cell line is useful to propagate a replication-defective HSV-2 vaccine strain that contains mutations and/or deletions in the ICP8 and UL5 genes.

13 Claims, No Drawings

HERPES VIRUS COMPLEMENTING CELL LINE

CROSS-REFERENCE TO RELATED APPLICATION

This application claims priority to U.S. provisional application No. 60/196,801, filed Apr. 13, 2000.

FIELD OF THE INVENTION

The present invention is in the fields of cellular and molecular biology. Specifically, The present invention is directed to a cell line useful for the growth of a mutant strain of Herpesvirus.

BACKGROUND OF THE INVENTION

Herpesviridae is a large family of enveloped linear dsDNA-containing animal viruses. Herpesviruses are morphologically similar. The virion (~120–200 nm diam.) contains a core (DNA wound around a central protein structure) within an icosahedral capsid (~100–110 nm diam.) comprising 12 pentameric and 150 hexameric capsomers. The viron is enclosed by a lipoprotein envelope bearing surface projections. The linear dsDNA genome characteristically contains repeated terminal and/or internal sequences.

Herpesviruses have been isolated from a wide range of animals, including mammals, birds, reptiles, amphibians, and fish. Many herpesviruses cause disease in their primary host(s), and may remain latent within the tissue of the host, often for life. Virus transmission commonly occurs by direct contact of mucosal surfaces. Some herpesviruses can be transmitted via body fluids (e.g., milk; via the placenta; etc).

Herpes simplex virus (HSV) type 1 or 2 is a causative agent for serious infections in humans. Herpes simplex diseases are characterized by the formation of thin-walled vesicles, which ulcerate, crust and heal; the vesicles occur, often in clusters, on skin and/or mucous membranes. Transmission occurs as a result of close physical contact; e.g., sexual contact, kissing, close contact sports such as wrestling (*Herpes gladiatorum*). HSV incubation periods range from 2–12 (average 6) days. The disease state varies from subclinical to severe, and is occasionally fatal. HSV can remain latent in nerve cells near the site of infection. Reactivation may occur spontaneously or in response to other infections (e.g., stress, immunosuppression). In neonates and immunodeficient individuals, HSV may become-disseminated; often affecting the liver, adrenal glands, brain, etc.

HSV-2 is associated with genital, and hence neonatal, infections (*Herpes genitalis*), and is a disease of significant morbidity in infected individuals (Whitley, 1996). In addition to the conditions described above, other symptoms may include e.g. fever, dysuria, pain, and malaise. In women, the cervix is often the main site of genital infection (herpetic cervicitis). HSV-2 infection in women is associated with an increased risk of abortion and of cervical cancer. Individuals with active HSV-2 have an increased risk of acquiring HIV if exposed to the virus (Augenbraun and McCormack).

Neonatal herpes is usually acquired (during birth) from a mother infected with HSV-2. Fatality rates may be 50% or more in untreated cases. Surviving infants commonly show neurological and/or ocular secondary disorders.

Clinical diagnosis of HSV-2 infection is established by microscopic examination of lesion samples, or biopsies from e.g. skin, brain or liver for multinucleate giant cells with eosinophilic intranuclear inclusion bodies, or by various immunofluorescence techniques (e.g., ELISA).

A number of antiviral agents (e.g. vidarabine, acyclovir, IDU and trifluorothymidine) have activity against HSV and may be effective in some cases (e.g. vidarabine is used against HSV encephalitis). These drugs are not generally effective in preventing recurrence or transmission, however. There remains an unmet need for an effective vaccine against HSV-2 to induce protective immunity and to prevent or to reduce primary infection and, ideally, to reduce recurrent disease and transmission.

Numerous approaches have been attempted to obtain immunization against HSV infection (e.g., glycoprotein subunits, inactivated virus, attenuated virus, and various HSV antigens. See Krause and Straus, 1999; Bernstein and Stanberry, 1999; and Stanberry, 1998). These approaches have shown little to no effectiveness, however (e.g., HSV glycoprotein subunit vaccines, Corey et al., 1999 and Straus et al, 1997; attenuated HSV, Cadoz, et al., 1992).

The use of replication-defective mutant viral strains is a promising avenue of induced immunization against HSV in animal models (Boursnell et al., 1997; Da Costa et al., 1997; Farrell et al., 1994; McLean et al., 1994; McLean, 1996; Morrison and Knipe, 1994; Morrison, Da Costa, and Knipe, 1998; Nguyen et al., 1992; and Stanberry, 1999). Current studies, however, use single mutant viruses, which carry with it the threat of back mutation (reversion to a virulent wild type). Standard vaccine design typically utilizes strains with two or more (non-reverting) mutations to increase safety of the vaccine (Curtiss et al., 1994).

In an effort to develop a live mutant virus vaccine, while reducing the risk of reversion, Da Costa et al. have developed a double deletion mutant HSV-2 strain. This strain lacks two genes essential for DNA replication, thus rendering the mutant incapable of DNA synthesis and viral replication. This double deletion mutant virus strain fails to form plaques or to give any detectable single cycle yields in normal monkey or human cells, yet it is capable of eliciting an immune response (i.e., it functions as an effective immunogen). This double deletion mutant HSV-2 strain induces antibody titers in mice equivalent to those induced by single deletion mutant viruses (Da Costa et al., manuscript submitted).

Because this double deletion mutant HSV-2 strain is replication defective, the replication gene product components it lacks must be provided. There is a need, therefore, for a cell line capable of complementing this double deletion mutant HSV-2 strain, enabling the propagation of the strain, thus providing vaccine production level growth stock of the mutant strain.

SUMMARY OF THE INVENTION

The present invention is directed to a cell line capable of supporting replication of a growth-defective Herpes Simplex Virus strain; specifically a replication-defective HSV-2 double mutant. This complementing cell line provides a means to propagate a growth defective strain of HSV useful as, for example, stock immunogen for vaccine production.

In one preferred embodiment, the present invention is directed to a cell line that expresses the ICP8 protein and the UL5 protein of Herpes Simplex Virus. This cell line is useful to propagate a replication-defective HSV-2 vaccine strain that contains mutations and/or deletions in the ICP8 and UL5 genes. Most preferably, the complementing cell line exhibits the characteristics of the complementing cell line as deposited with the American Type Cell Culture (ATCC) and assigned the Patent Deposit Designation PTA-2403.

In another embodiment of the invention the UL5/ICP8 expressing cell line contains an ICP8/UL5-defective HSV-2 strain.

Another embodiment of the present invention is directed to a method for producing an ICP8/UL5-defective HSV-2 strain by propagating the mutant virus using the UL5/ICP8 expressing cell line, and harvesting the virus resulting from the cell culture.

In one aspect of the present invention, the complementing cell line reduces the possibility of reversion of the defective virus to its wild type form during replication in the complementing cell line. This is achieved by assuring the complementing cell line contains minimal sequence homology with the replication-defective HSV strain to avoid genetic recombination and to produce only defective virus. This aspect is of added benefit because a complementing cell line with little or no sequence homology with a mutant HSV strain provides further safety during growth of the virus.

DETAILED DESCRIPTION OF THE INVENTION

Vero Cells (African Green Monkey Kidney Cells, ATCC #81-CCL) were used to create a cell line that expresses the UL5 and ICP8 proteins of Herpes Simplex Virus. It is understood, however that any of a variety of suitable cell lines may be used in the practice of this invention.

As an initial step, suitable expression vectors for each of the defective viral genes are created by any of a variety of techniques known in the art and using any of a number of suitable vectors.

Then, a cell line capable of expressing one of the two defective viral genes is created, using any of a variety of genetic engineering techniques known in the art For example, an ICP8 expressing cell line may be generated by transfecting Vero cells with an HSV-1 ICP8 expression plasmid. A modified calcium phosphate method of transfection may be used to create the ICP8 expressing cell line. As described herein, the ICP8 expression plasmid, pRC/CMV-ICP8-A1(RA1) may be used in the construction of this cell line.

Finally, the cell line capable of expressing the first of the two defective viral genes is manipulated to express the second of the two defective viral genes. For example, an ICP8 expressing cell line may be further transfected with a UL5 expression plasmid using, for example, an electroporation method of transfection. As described herein, the UL5 expression plasmid, p70-4 is useful in this transfection.

An ICP8/UL5 expressing cell line is selected on the basis of its ability to support the replication of both an ICP8 mutant HSV-2 strain, and a UL5 mutant HSV-2 strain.

Many component steps of the present invention may be performed by alternative, yet functionally equivalent, biochemical or genetic engineering techniques known in the art without altering the inventive nature of the present disclosure. For example, methods for generating recombinant nucleic acids, vector construction, host cell transformation, polypeptide expression systems, and phage display useful in the practice of this invention can involve a wide variety of modern genetic engineering techniques, tools, and biological sources that are well known in the art and routinely practiced by those skilled in the art. Exemplary techniques and methods are described in detail herein by way of preferred example, but are not limiting to the practice of the invention. The present invention incorporates by reference in their entirety techniques and supplies well known in the field of molecular biology, including, but not limited to, techniques and supplies described in the following publications:

Ausubel, F. M. et al. eds., *Short Protocols In Molecular Biology* (4th Ed. 1999) John Wiley & Sons, NY. (ISBN 0-471-32938-X).

Freshney, R. I. *Culture of Animal Cells* (1987) Alan R. Liss, Inc.

Old, R. W. & S. B. Primrose, *Principles of Gene Manipulation: An Introduction To Genetic Engineering* (3d Ed. 1985) Blackwell Scientific Publications, Boston. Studies in Microbiology; V.2:409 pp. (ISBN 0-632-01318-4).

Sambrook, J. et al. eds., *Molecular Cloning: A Laboratory Manual* (2d Ed. 1989) Cold Spring Harbor Laboratory Press, NY. Vols. 1–3. (ISBN 0-87969-309-6).

Winnacker, E. L. *From Genes To Clones: Introduction To Gene Technology* (1987) VCH Publishers, NY (translated by Horst Ibelgaufts). 634 pp. (ISBN 0-89573-6144).

It will be readily apparent to those skilled in the art that other suitable modifications and adaptations of the compositions and methods of the invention described herein are obvious and may be made without departing from the scope of the invention or the embodiments disclosed herein. Having now described the present invention in detail, the same will be more clearly understood by reference to the following examples, which are included for purposes of illustration only and are not intended to be limiting of the invention.

Each of the publications mentioned herein is incorporated by reference.

EXAMPLE 1

Preparation of Reagents and Solutions

Penicillin/Streptomycin Solution, 200×

200× Penicillin/Streptomycin was prepared as follows: A 0.9% NaCl solution was prepared by dissolving 0.9 g of NaCl in 100 ml of sterile deionized water. 200× Penicillin/Streptomycin solutions were prepared by separately dissolving the contents of two bottles of penicillin/streptomycin base (Sigma, #P-3539, 5 g) in 50 ml of the 0.9% NaCl solution. The two 50 ml Penicillin/Streptomycin solutions were combined and filter sterilized using 0.2 μM (100 ml capacity) filter units. The 200× Penicillin/Streptomycin solutions were divided into 10 ml aliquots and dispensed into sterile test tubes (15 ml capacity). The solutions were stored at −20° C. and thawed at room temperature prior to use.

Larger laboratory stock of 200× Penicillin/Streptomycin was prepared as follows: Two 500 ml aliquots of PBS were filter sterilized using separate 0.2 μM filter units (500 ml capacity) prior to use. 200× Penicillin/Streptomycin solutions were prepared by separately dissolving the contents of two bottles of penicillin/streptomycin base (Sigma, #P-3539, 5 g) in 50 ml of sterile phosphate buffered saline, pH 7.4 (PBS). The two 50 ml Penicillin/Streptomycin solutions were combined and filter sterilized using 0.2 μM (100 ml capacity) filter units. The 200× Penicillin/Streptomycin solutions were divided into 10 ml aliquots and dispensed into sterile test tubes (15 ml capacity). The solutions were stored at −20° C. and thawed at room temperature prior to use.

Gentamicin (G418) Solution, 100 mg/ml

The microbial potency (active G418) for the lot of material was obtained from the supplier's information provided with the material. The amount of diluent required to prepare a solution having a potency of 100 mg/ml active G418 was determined as follows:

Microbial potency=740 µg/mg 740 µg/mg×5000 mg (contents of bottle)=3700 mg active G418

(3700 mg active G418)/(xml of diluent)=100 mg active G418 (final concentration)/(1 ml)

x(ml of diluent)=37 ml DMEM 12 ml of Dulbecco's Modified Eagles Medium (DMEM) was added to 5 g of G418 and dissolved by repeat pipetting. An additional 12 ml of DMEM was added to dissolve any remaining G418 powder. The final volume of the G418 solution was adjusted to 37 ml with DMEM. The solution was mixed by inversion and dispensed into sterile test tubes in 5 ml aliquots. The G418 solution aliquots were stored at −20° C. and thawed at room temperature prior to use.

Fetal Bovine Serum, Heat Inactivated

Fetal bovine serum used as a cell culture media additive was heat inactivated. Bottles containing 100 ml of fetal bovine serum were stored at −20° C. Prior to use, a bottle of serum was placed in a 37° C. water bath until the contents of the bottle had thawed. The bottle was then transferred into a 56° C. water bath for 30 minutes. The heat inactivated serum was then used to prepare cell culture media.

Cell Culture Media:

V Media

The cell culture media designated "V" Media was prepared by adding the following to a bottle containing 500 ml of DMEM: 55 ml of fetal bovine serum, heat inactivated; 2.8 ml 200× Penicillin/Streptomycin solution. The contents of the bottle were mixed by swirling the bottle. The prepared media was stored at 4° C. between uses.

G Media

The cell culture media designated "G" Media was prepared by adding the following to a bottle containing 500 ml of DMEM: 55 ml of fetal bovine serum, heat inactivated; 2.8 ml 200× Penicillin/Streptomycin solution; 2.8 ml of 100 mg/ml G418 solution. The contents of the bottle were mixed by swirling the bottle. The prepared media was stored at 4° C. between uses.

S2 Media

The cell culture media designated "S2" Media was prepared by adding the following to a bottle containing 500 ml of DMEM: 55 ml of fetal bovine serum, heat inactivated; 2.8 ml 200× Penicillin/Streptomycin solution; 1.1 ml of 100 mg/ml G418 solution. The contents of the bottle were mixed by swirling the bottle. The prepared media was stored at 4° C. between uses.

S2Z Media

The cell culture media designated "S2Z" Media was prepared by adding the following to a bottle containing 450 ml of DMEM (50 ml of DMEM removed from bottle containing 500 ml): 50 ml of fetal bovine serum, heat inactivated; 2.5 ml 200× Penicillin/Streptomycin solution; 1.0 ml of 100 mg/ml G418 solution; 2.5 ml of 100 mg/ml Zeocin solution. The contents of the bottle were mixed by swirling the bottle. The bottle containing the prepared media was wrapped in aluminum foil and stored at 4° C. between uses.

Freezing Media

Freezing media was prepared by mixing equal volumes of DMEM with heat inactivated fetal bovine serum.

Transfections Solutions:

2× HBS (Hepes Buffered Saline)

2× HBS was prepared immediately prior to use by dissolving Hepes salt, NaCl and $Na_2HPO_4$ in 100 ml of sterile, distilled and deionized water as follows:

|  |  | Final Concentration |
| --- | --- | --- |
| Hepes Salt (FW = 260.3 g) | 1.3 g | 50 mM |
| NaCl (FW = 58.4 g) | 1.6 g | 280 mM |
| $Na_2HPO_4$ (FW = 141.96) | 0.02 g | 1.5 mM |

The 2× HBS solution was filter sterilized using a 0.2 µM filter unit prior to use.

1× HBS (Hepes Buffered Saline)

1× HBS was prepared immediately prior to use by dissolving Hepes salt, NaCl and $Na_2HPO_4$ in 100 ml of sterile, distilled and deionized water as follows:

|  |  | Final Concentration |
| --- | --- | --- |
| Hepes Salt (FW = 260.3 g) | 0.65 g | 25 mM |
| NaCl (FW = 58.4 g) | 0.8 g | 140 mM |
| $Na_2HPO_4$ (FW = 141.96) | 0.01 g | 0.75 mM |

The 1× HBS solution was filter sterilized using a 0.2 µm filter unit prior to use.

2M $CaCl_2$

2M $CaCl_2$ was prepared immediately prior to use by dissolving 2.94 g of $CaCl_2$ (FW=147.02) in 10 ml of sterile, distilled and deionized water. The 2M $CaCl_2$ solution was filter sterilized using a 0.2 µm filter unit prior to use.

EXAMPLE 2

Construction of an ICP8 Expression Vector: PRC/CMV-ICP8-A1(RA1)

The open reading frame (ORF) of the UL29 gene was inserted into the commercial vector, pRc/CMV (Invitrogen Corporation, Carlsbad, Calif.,) in order to construct a plasmid that could express the protein, ICP8.

The UL29-ORF was constructed using polymerase chain reaction (PCR) amplification techniques known in the art. PCR primers were designed to allow amplification of the ORF of the UL29 gene only. Unique restriction sites were engineered into the 5' ends of the primers for directional cloning of the PCR product into the commercial vector.

After amplifying the ORF, the blunt ended PCR product was cloned into the EcoRV site of pBluescript II SK ASK) to generate pSK/UL29-ORF. The UL29-ORF was subsequently cut out from pSK/UL29-ORF with HindII and XbaI, and cloned into the multiple cloning site of pRc/CMV to generate the ICP8 expression plasmid.

The ICP8 expression plasmid contains the CMV immediate early enhancer/promoter, the open reading frame (ORF) from the UL29 gene, and the bovine growth hormone polyA signal. The plasmid also contains the ampicillin resistance gene for preparation of the plasmid in bacteria, and the neomycin resistance gene for selection of stable eukaryotic cell lines.

This ICP8 expression plasmid was designated pRC/CMV-ICP8-A1(RA1)

EXAMPLE 3

Construction of a UL5 Expression Vector: P70-4

The open reading frame of the ULS gene from Herpes Simplex virus type 2 (HSV-2) was amplified using PCR techniques. A plasmid containing the UL5 gene cloned from HSV-2 was used as a template for the PCR amplification.

Plasmid pEH49 contains a 7.6 Kb EcoRI-HindIII fragment of HSV 2 DNA containing the UL5 gene. A 3327 bp KpnI-MluI sub fragment from pEH49 was cloned into the vector PSL1190, resulting in plasmid pUL5 (obtained from Xavier Da Costa, Harvard Medical School).

The HSV-2 DNA present in pUL5 was sequenced and compared to the published sequence of ULS to enable the selection of primers to be used in the PCR amplification of the UL5 open reading frame. Restriction sites were engineered into the 5' ends of the primers for directional cloning of the PCR product into a commercially available vector.

The PCR amplification of the ULS open reading frame yielded a 2.6 Kb fragment that was cloned into the pCRP™ 2.1 cloning vector (Invitrogen Corporation, Carlsbad, Calif.,). A 2.6 Kb HindIII-NotI fragment was subcloned from the pCR™ 2.1 cloning vector into the constitutive mammalian expression vector pZeoSV2 (Invitrogen Corporation, Carlsbad, Calif.,). The pZeoSV2 expression vector contains the gene that confers resistance to the antibiotic Zeocin™ and the bovine growth hormone polyA signal. The expression of the UL5 gene product is under the control of the SV40 early enhancer/promoter.

The resulting plasmid was designated p70-4.

EXAMPLE 4

Construction of an ICP8 Expressing Cell Line: VRA1

Vero Cells (African Green Monkey Kidney Cells, ATCC #81-CCL) were used to create a cell line that expresses the ICP8 proteins of Herpes Simplex Virus by transfecting Vero cells with the HSV-1 ICP8 expression plasmid, pRC/CMV-ICP8-A1(RA1), described in example 2. A modified calcium phosphate method of transfection was used to create the ICP8 expressing cell line.

Four ampules of Vero Cells were removed from liquid nitrogen storage. The ampules were placed in a 37° C. water bath to rapidly thaw the contents. The thawed cell suspensions were transferred to a sterile test tube containing chilled Dulbecco's Modified Eagle's Medium (DMEM). The cells were harvested by centrifugation at 10,000 rpm for 10 minutes at 40° C. in a Sorvall RT 6000D centrifuge. The supernatant was removed from the cell pellet and the cells were gently re-suspended in "V" media.

The cell suspension was transferred to a T25 cell culture flask. The cells were fed and split through a series of passages using standard tissue cell culture procedures and materials known in the art. The cells were harvested at each passage by dissociating the cells from the culture vessel with trypsin. The continuous culture and expansion of the Vero cells was continued, resulting in a total of twenty two passages. Cell monolayers of the Vero cells at passage 22 (P22) were prepared in 6 cm cell culture plates for transfection with the ICP8 expression plasmid pRC/CMV-ICP8-A1(RA1).

A solution containing 1.4 $\mu$g of plasmid DNA was prepared by adding 4 $\mu$l of the plasmid preparation (DNA concentration=0.35 $\mu$g/$\mu$l) to 259 $\mu$l of sterile water in a sterile epindorf tube. A solution containing 8 $\mu$g of plasmid DNA was prepared by adding 22.9 $\mu$l of the plasmid preparation (DNA concentration=0.35 $\mu$g/$\mu$l) to 240.1 $\mu$l of sterile water in a sterile epindorf tube. The contents of the tubes were mixed by vortexing. 37 $\mu$l of 2M $CaCl_2$ was added to each solution and mixed by vortexing.

300 $\mu$l of 2×HBS was added to two sterile polypropylene test tubes. To prepare the DNA transfection solutions, the plasmid DNA/$CaCl_2$ solutions were added dropwise to the 300 $\mu$l of 2×HBS. The polypropylene tubes containing the 2×HBS were vortexed during the addition of the DNA/$CaCl_2$ solutions. The DNA transfection solutions were incubated for 30 minutes at room temperature and then vortexed.

The solutions were separately added dropwise to two 6 cm plates of P22 Vero cells. The plates containing the cell monolayers and plasmid DNA transfection solutions were placed in a 37° C/5% $CO_2$ incubator for 24 to 48 hours.

The cell culture plates containing the transfected Vero cells were removed from the incubator and the media was removed from the plate. The cell monolayers were washed by adding 4 ml of PBS to each plate, swirling the plate for 1 minute and then decanting the PBS off the plate. 3 ml of trypsin was added to each plate, the plates were swirled to distribute the trypsin and the trypsin was poured off the plates. The plates were placed in a 37° C./5% $CO_2$ incubator for 5–10 minutes.

V Media was added to ten (10), 10 cm cell culture plates (9.5 ml/plate). The plates containing the trypsinized cells were removed from the incubator and the plates were tapped to dislodge the cells from the bottom of the plate. 2.5 ml of V media was added to each plate. The cells were re-suspended in the media with gentle repeat pipetting. The re-suspended cells were transferred in 0.5 ml aliquots to the 10 cm cell culture plates containing 9.5 ml of V media. 100 $\mu$l of G418 solution (100 mg/ml) was added to each 10 cm cell culture plate. The plates were incubated in a 37° C./5% $CO_2$ incubator for approximately four days.

The 10 cell culture plates containing the transfected Vero cells were removed from the incubator. The media was poured off the plates and 10 ml of G media was added to each plate. The plates were returned to the 37° C./5% $CO_2$ incubator for an additional 9 days.

Individual colonies of G418 resistant Vero cells were selected and transferred to individual wells of 24-well cell culture plates. The 10 cell culture plates containing the transfected Vero cells were removed from the incubator. The plates were vigorously swirled to dislodge any dead cells from the bottom of the plate. The media containing dead cells was poured off the plates. The remaining cell colonies in each plate were washed with 5 ml of PBS. Individual cell colonies were visualized and separately "picked". Colonies were picked by adding 2 $\mu$l of trypsin directly to the colony. The cells were then gently scraped from the plate using a pipette tip. The cells were transferred into a well of a 24-well cell culture plate containing 0.5 ml of G media. The 24-well cell culture plates were placed in a 37° C./5% $CO_2$ incubator for approximately 9 days.

The selected G418 resistant cells were transferred from the 24-well cell culture plates to 6-well cell culture plates. The 24-well cell culture plates were removed from the incubator. The media was aspirated from the wells. 1 ml of Dulbecco's Modified Eagles Medium (DMEM) was added to each well. The DMEM was aspirated from the wells after approximately 1 minute of incubation. To each well 0.5 ml of trypsin was added. The plates were swirled and the trypsin was aspirated from the wells. The plates were incubated for 5–10 minutes in a 37° C./5% $CO_2$ incubator. The plates were removed from the incubator and tapped to detach cells from the wells of the plate. The cells in each well were re-suspended in 1 ml of G media. The cell suspensions from individual wells were transferred to wells of a 6-well cell culture plate containing 1 ml of G media. The 6-well plates were placed in a 37° C./5% $CO_2$ incubator for approximately 4 days.

The selected G418 resistant cells were transferred from the 6-well cell culture plates to T25 cell culture flasks. The 6-well cell culture plates were removed from the incubator. The media was aspirated from the wells. 2 ml of Dulbecco's Modified Eagles Medium (DMEM) was added to each well. The DMEM was aspirated from the wells after approximately 1 minute of incubation. To each well 0.5 ml of trypsin was added. The plates were swirled and the trypsin was aspirated from the wells. An additional 200 µl of trypsin was added to each well. The plates were tapped to detach cells from the wells of the plate. The cells in each well were re-suspended in 1 ml of G media. The cell suspensions from individual wells were transferred to separate T25 cell culture flasks containing 5 ml of G media. The T25 flasks were placed in a 37° C./5% $CO_2$ incubator for approximately 6 days. The T25 cell culture flasks containing the selected G418 resistant cells were removed from the incubator. The media was removed from the flask and the cells were washed with 6 ml of PBS. Trypsin was added to each flask (3 ml). The flasks were placed on their sides for 30 seconds to allow the trypsin to be distributed over the cell monolayer. The trypsin was decanted from the flask. Three (3) ml of G media was added to each flask and the flasks were tapped to dislodge the cells. Aliquots of the cell suspensions were transferred to wells of 6-well cell culture plates containing 1 ml of G media. From each T25 flask two, 1.25 ml aliquots of the cell suspension were transferred to individual wells of a 6-well plate. The 6-well cell culture plates were prepared for the screening of G418 resistant Vero cell clones for their ability to support replication of the HSV-2 ΔICP8 Strain A1-1 (provided by David Knipe). The cell culture plates were placed in a 37° C./5% $CO_2$ incubator. 5.5 ml of G media was added to each cell suspension remaining in the T25 flask (~0.5 ml) and the flasks were returned to the incubator.

EXAMPLE 4.1

Screening of ICP8 Expressing Cell Line VRA1 to Confirm G418 Resistance

Vero cells transfected with the ICP8 expression vector pRC/CMV-ICP8-A1(RA1), described in example 4, were grown in the presence of G418 to select for transfected cells based on G418 resistance conferred by the expression vector. The Vero cells transfected with a solution containing 8 µg of plasmid DNA yielded 27 individual G418 resistant colonies that were selected and expanded.

EXAMPLE 4.2

Screening of ICP8 Expressing Cell Line VRA1 for the Ability to Support Replication of HSV-2 ΔICP8 Strain A1-1

HSV-2 strain ΔICP8 A1-1 contains a mutation on the UL29 gene and does not express the ICP8 protein. A laboratory virus stock preparation of HSV-2 strain ΔICP8 A1-1, passage 3 was removed from frozen storage. The ampule containing the viral stock was thawed in a 37° C. water bath and placed on ice. The viral stock was diluted as follows:

Viral stock ΔICP8 A1-1 diluted 1:30,000:
Dilution #1: 50 µl viral stock+4.95 ml DPBS
Dilution #2: 50 µl Dilution #1+4.95 ml DPBS
Dilution #3: 2.0 ml Dilution #2+4.0 ml DPBS VRA1 cell monolayers, as described earlier, were washed with 2 ml of PBS. Each of six wells was inoculated with 200 µl of the diluted ΔICP8 A1-1 virus preparation. In addition, cell monolayers of the ICP8 expressing cell line JW73A (Avant Immunotherapeutics, Inc., Needham, Mass.) were inoculated with 200 µl of the diluted ΔICP8 A1-1 virus preparation as a positive control for the plaque assay. The plates were placed in a 37° C./5% $CO_2$ incubator and rocked every ten minutes for 60 minutes. 2 ml of Media 199 (Gibco Life Technologies, Rockville, Md.; including fetal calf serum, penicillin/streptomycin solution, gamma globulin, and glutamine) was added to each well and the plates were incubated for 2 days. The plates were removed from the incubator and the wells were observed for the presence of plaques.

Clones were scored as positive for ICP8 expression based on the number and the size of resulting plaques, as compared to the positive control cell line. A single clone (VRA1) was selected based on these criteria. The tissue culture plate wells containing the clone and the positive control cell line JW73A had ~200–400 plaques of comparable size and morphology.

The G418 resistant clone (VRA1), positive for its ability to support replication of HSV-2 ΔICP8 strain A1-1, was expanded and a frozen stock was prepared. A T25 cell culture flask containing the VRA1 cell line incubated for approximately 3 days. The media was removed from the flask and the cell monolayer was washed with 6 ml of PBS. The cells were detached with trypsin and re-suspended in 3 ml of G media. The cell suspension was divided into three, 1 ml aliquots. Each 1 ml aliquot was transferred to a T75 cell culture flask containing 12 ml of G media and incubated for approximately four days.

After incubation, media was poured from the flasks and the cell monolayers were washed with PBS. The cells were detached with trypsin and re-suspended in G media. The cell suspension was divided into two aliquots. Each aliquot was transferred to a T150 cell culture flask containing G media. The T150 flasks were placed in a 37° C./5% $CO_2$ incubator for an additional two days.

Following incubation, the media was removed from the flasks and the cell monolayers were washed with PBS. The cells were detached with trypsin and re-suspended in 6 ml of DMEM containing 10% fetal bovine serum. Two T75 cell culture flasks containing 12 ml of G media were inoculated with 0.5 ml of the cell suspension. The flasks were placed in a 37° C./5% $CO_2$ incubator. The remaining cell suspensions were transferred to a single sterile polypropylene centrifuge tube and the volume was adjusted to 20 ml with DMEM.

The cell suspension was centrifuged for 10 minutes at 4° C. at 1000 RPM in a Sorvall RT 6000D centrifuge. The supernatant was removed from the cell pellet and the cells were re-suspended in 2 ml of freezing media. To the 2 ml cell suspension a solution of DMEM containing 10% DMSO was added to a total volume of 4 ml. The cell suspension was slowly mixed with a pipette and 1 ml aliquots were transferred to sterile cryovials. The cryovials were placed in a styrofoam box and were placed in a −20° freezer. The cryovials were transferred to vapor phase liquid nitrogen storage the following day.

EXAMPLE 5

Construction of a UL5/ICP8 Expressing Cell Line: V295

The ICP8 expressing VRA1 cell line from example 4.2 was transfected with the UL5 expression plasmid p70-4 (described in example 3) by electroporation.

Cell monolayers of VRA1 were grown in T150 flasks. The cell monolayers were washed with 25 ml PBS. The cell monolayers were coated with trypsin and incubated for 30 seconds at room temperature. The cells were detached from the flask surface by tapping the flasks. The cells in each flask were re-suspended with 6 ml of S2 media.

Cell suspensions were combined in a single sterile polypropylene centrifuge tube. A 100 µl sample of the cell suspension was added to a test tube containing 900 µl PBS (1:10 dilution). The cell suspension was diluted 1:2 with trypan blue dye and the cell density was determined using a hemacytometer. The cell density was determined to be $1.9 \times 10^6$ cells/ml. The total number of cells in the cell suspension was calculated to be $2.3 \times 10^7$. The cell suspension was centrifuged for 10 minutes at 4° C. at 1000 RPM in a Sorvall RT 6000D centrifuge. The supernatant was removed from the cell pellet and the cells were re-suspended in 0.46 ml of 1×HBS (~$5 \times 10^7$ cells /ml).

A mixture of VRA1 cells and p70-4 plasmid DNA was prepared for electroporation. A 200 µl sample of the cell suspension was transferred to an epindorf tube. 3 µl of laboratory stock plasmid p70-4 was added to the cell suspension. 12 µl of 10% dextrose was added to the tube and the volume was adjusted to 800 µl using 1× HBS. The cell suspension was mixed and transferred to an electroporation cuvette.

The electroporator was set at 960 µFd and 0.25 volts. The cuvette was placed in the electroporator and pulsed as per instructions located in the electroporation apparatus operating manual. Following electroporation, the cuvette was placed on ice. The contents of the electroporation cuvette were transferred to a 10 cm cell culture plate containing 10 ml V media. The plate was placed in a 37° C./5% $CO_2$ incubator for approximately 2 days.

After incubation, the cell culture plate containing the electroporated VRA1 cell monolayer was washed by adding 10 ml of PBS to the plate, swirling the plate for 1 minute and then decanting the PBS off the plate. Five (5) ml of trypsin was added to the plate, the plate was swirled to distribute the trypsin and the trypsin was poured off the plate. An additional 500 µl of trypsin was added to the plate. S2Z Media was added to ten, 10 cm cell culture plates (9.5 ml/plate). The plates containing the trypsinized cells were removed from the incubator and the plates were tapped to dislodge the cells from the bottom of the plate. 5.0 ml of S2Z media was added to each plate. The cells were re-suspended in the media with gentle repeat pipetting. The re-suspended cells were transferred in 0.5 ml aliquots to the 10 cm cell culture plates containing 9.5 ml of S2Z media. The plates were incubated in a 37° C./5% $CO_2$ incubator for an additional 12 days.

Following incubation, individual colonies of Zeocin resistant VRA1 cells were selected and transferred to individual wells of 24 well cell culture plates. The 10 cell culture plates containing the transfected Vero cells were removed from the incubator. The plates were vigorously swirled to dislodge any dead cells from the bottom of the plate. The media containing dead cells was poured off the plates. The remaining cell colonies in each plate were washed with 5 ml of PBS. Individual cell colonies were visualized and separately "picked". Colonies were picked by adding 3 µl of trypsin directly to the colony. The cells were then gently scraped from the plate using a pipette tip. The cells were transferred into a well of a 24-well cell culture plate containing 0.5 ml of S2Z media. The 24-well cell culture plates were placed in a 37° C./5% $CO_2$ incubator for approximately six days.

The selected Zeocin resistant VRA1 cells were transferred from the 24-well cell culture plates to 6-well cell culture plates. The 24-well cell culture plates were removed from the incubator. The media was aspirated from the wells. 1 ml of Dulbecco's Modified Eagles Medium (DMEM) was added to each well. The DMEM was aspirated from the wells after approximately 1 minute of incubation. To each well 0.5 ml of trypsin was added. The plates were swirled and the trypsin was aspirated from the wells. The plates were incubated for 5–10 minutes in a 37° C./5% $CO_2$ incubator. The plates were removed from the incubator and tapped to detach cells from the wells of the plate. The cells in each well were re-suspended in 1 ml of S2Z media. The cell suspensions from individual wells were transferred to wells of a 6-well cell culture plate containing 1 ml of S2Z media. The 6-well plates were placed in a 37° C./5% $CO_2$ incubator for approximately six days.

The selected Zeocin resistant VRA1 cells were transferred from the 6-well cell culture plates to T25 cell culture flasks. The 6-well cell culture plates were removed from the incubator. The media was aspirated from the wells. 2 ml of Dulbecco's Modified Eagles Medium (DMEM) was added to each well. The DMEM was aspirated from the wells after approximately 1 minute of incubation. To each well 0.5 ml of trypsin was added. The plates were swirled and the typsin was aspirated from the wells. An additional 200 µl of trypsin was added to each well. The plates were tapped to detach cells from the wells of the plate. The cells in each well were re-suspended in 1 ml of G media. The cell suspensions from individual wells were transferred to separate T25 cell culture flasks containing 5 ml of S2Z media. The T25 flasks were placed in a 37° C./5% $CO_2$ incubator for approximately 4 days.

The T25 cell culture flasks containing the selected G418 resistant cells were removed from the incubator. The media was removed from the flasks and the cells were washed with 6 ml of PBS. Trypsin was added to each flask (3 ml). The flasks were placed on their sides for 30 seconds to allow the trypsin to be distributed over the cell monolayer. The trypsin was decanted from the flask. 3 ml of S2Z media was added to each flask and the flasks were tapped to dislodge the cells. Aliquots of the cell suspensions were transferred to wells of 6-well cell culture plates containing 1 ml of S2Z media. From each T25 flask two, 1.25 ml aliquots of the cell suspension were transferred to individual wells of a 6-well plate.

The 6-well cell culture plates were prepared for the screening of Zeocin resistant VRA1 cell clones for their ability to support replication of the HSV-2 ΔICP8 Strain A1-1 and the HSV-2 ΔUL5 Strain Hr99 (provided by David Knipe). The cell culture plates were placed in a 37° C./5% $CO_2$ incubator. 5.5 ml of S2Z media was added to each cell suspension remaining in the T25 flask (~0.5 ml) and the flasks returned to the incubator.

EXAMPLE 5.1

Screening of UL5/ICP8 Expressing Cell Line V295 to Confirm G418/Zeocin Resistance VRA1 cells electroporated with the UL5 expression vector p70-4 were grown in the presence of the antibiotics G418 and Zeocin to select for cells bearing both of the expression vectors. Of the G418/Zeocin resistant colonies that arose following passage of the transfected cells in media containing G418 and Zeocin, 150 colonies were selected and expanded.

EXAMPLE 5.2

Screening of UL5/ICP8 Expressing Cell Lien V295 for the Ability to Support Replication of HSV-2 ΔICP8 Strain A1-1 and HSV-2 ΔUL5 Strain HR99

The ICP8/UL5 expressing V295 cell line was selected on the basis of it's ability to support the replication of both an ICP8 mutant HSV-2 strain, and a UL5 mutant HSV-2 strain and a frozen stock prepared.

HSV-2 strain ΔICP8 A1-1 contains a mutation on the UL29 gene and does not express the ICP8 protein. HSV-2 strain ΔUL5 Hr99 contains a mutation in the UL5 gene and does not express the UL5 protein. Laboratory virus stock preparations of HSV-2 strain ΔICP8 A1-1, passage 2 and HSV-2 strain ΔUL5 Hr99 were removed from frozen storage. Ampules containing the viral stocks were thawed in a 37° C. water bath and placed on ice. The viral stocks were diluted as follows:

HSV-2 strain ΔICP8 A1-1 P2 stock (titer=$4.6 \times 10^7$ pfu/ml) diluted 1:23,000:

Dilution #1 (1: 1000): 5 μl viral stock+5.0 ml DPBS

Dilution #2 (1:23): 625 μl Dilution #1+14.3 ml DPBS

HSV-2 strain ΔUL5 Hr99 stock (titer=$1.6 \times 10^8$ pfu/ml) diluted 1:80,000:

Dilution #1 (1:1000): 5 μl viral stock+5.0 ml DPBS

Dilution #2 (1:80): 188 μl Dilution #1+14.8 ml DPBS

Zeocin/G418 resistant VRA1 cell monolayers, as described earlier, were washed with 2 ml of PBS. Each of six wells was inoculated with either a) 200 μl of the diluted ΔICP8 A1-1 virus preparation (~400 pfu), or b) 200 μl of the diluted ΔUL5 Hr99 virus preparation (~400 pfu). In addition, cell monolayers of the ICP8 expressing cell line JW73A and the UL5 expressing cell line L2-5 (obtained from Dr. David Knipe, Harvard Medical School) were each inoculated with 200 μl of their respective diluted virus preparation as positive controls for the plaque assay. The plates were placed in a 37° C./5% $CO_2$ incubator and rocked every ten minutes for 60 minutes. 2 ml of Media 199-0 was added to each well and the plates were incubated for 4 days. The plates were removed from the incubator and the wells were observed for the presence of plaques.

Clones were scored as positive for ICP8 and UL5 expression based on the number and the size of resulting plaques, as compared to the positive control cell lines. A single clone (V295) was selected based on these criteria. The results of the plaque assay for the V295 isolate are as follows:

| Cell Line | Infected with HSV-2 ΔICP8 Strain A1-1 | Infected with HSV-2 ΔUL5 Strain Hr99 | Negative Infection Control (PBS) |
|---|---|---|---|
| JW73A | ~200 plaques | 0 plaques | 0 plaques |
| L2-5 | 0 plaques | ~200 plaques | 0 plaques |
| V295 | ~200 plaques | ~200 plaques | 0 plaques |

A Zeocin/G418 resistant cell line (V295, ATCC deposit PTA-2403), positive for its ability to support replication of HSV-2 ΔICP8 strain A1-1 and HSV-2 ΔUL5 strain Hr99 was expanded. The cell line was expanded through a series of passages using standard cell culturing methods. To transfer cells to new culture vessels at each passage, the culture media was removed from the culture vessel, the cells were washed with PBS and the cells were dissociated from the vessel using trypsin. Cell suspensions were transferred to new culture vessels containing an appropriate amount of S2Z culture media.

T150 cell culture flasks containing final passage (P10) ICP8/UL5 expressing cell line V295 were removed from the incubator. The media was removed from the flasks and the cell monolayers were washed with PBS. The cells were detached with trypsin and re-suspended in 5 ml of DMEM containing 10% fetal bovine serum. The cell suspensions were transferred to a single sterile polypropylene centrifuge tube and the volume was adjusted to 20 ml with DMEM.

The cell suspension was centrifuged for 10 minutes at 4° C. at 1000 RPM in a Sorvall RT 6000D centrifuge. The supernatant was removed from the cell pellet and the cells were re-suspended in 2 ml of freezing media. 4 ml of a solution of DMEM containing 10% DMSO was added to the cell suspension. The cell suspension was slowly mixed with a pipette and six, 1 ml aliquots were transferred to sterile cryovials. Four cryovials containing 0.5 ml of the cell suspension were prepared using the remaining 2 ml of cell suspension. The cryovials were placed in a styrofoam box and were placed in a −80° freezer. The cryovials were transferred to vapor phase liquid nitrogen storage the following day.

EXAMPLE 6

Sequence Homology between a Replication-defective HSV-2 Mutant and the UL5/ICP8 Expressing Cell Line The amount of DNA sequence homology between the UL5/ICP8 expressing cell line and the UL5/ICP8 double mutant virus, was analyzed by considering each deletion in the virus separately, and in the context of the corresponding genetic construct used to create the complementing cell line (UL5 and ICP8 expression vectors).

Genetic information used in assessing the mutations created in the double mutant HSV-2 vaccine strain was provided by Xavier De Costa and David Knipe. Two single, UL5 and ICP8, mutants of HSV-2 were constructed in Dr. Knipe's laboratory. Viral DNA from the ICP8 and UL5 defective viruses was co-transfected into a cell line capable of complementing both defects to isolate a virus defective in both UL5 and ICP8. Information about the constructed deletions in the UL5 and ICP8 deleted virus was obtained from sequencing data provided by David Knipe (Harvard Medical School).

EXAMPLE 6.1

Confirming Minimal DNA Sequence Homology between a UL5 Defective HSV-2 and the UL5/ICP8 Expressing Cell Line The 2900 bp deletion in UL5 ORF in the recombinant virus starts 104 bp into the ORF at the 5' end and extends 361 bp past the stop codon. A deletion of the first hundred nucleotides of the UL5 ORF would have also caused a deletion in the overlapping UL6 ORF. This 104 bp region represents the only region of sequence homology between the complementing cell line and the ICP8/UL5 double mutant virus.

EXAMPLE 6.2

Confirming Minimal DNA Sequence Homology between an ICP8 Defective HSV-2 and the UL5/ICP8 Expressing Cell Line The 3743 bp deletion of the HSV-2 ICP8 gene begins approximately 82 bp upstream of the 5' end of the ICP8 ORF and extends past the translational stop codon of ICP8 in the recombinant virus. There is no sequence homology between the UL29 sequence present in the complementing cell line and the ICP8/UL5 double mutant virus.

I claim:

1. A method for producing a replication-defective, ICP8/UL5-defective herpesvirus double mutant comprising the steps of:

(a) propagating said ICP8/UL5-defective herpesvirus using a cell line that is able to support the growth said virus; and (b) harvesting the virus resulting from step (a).

2. The method of claim 1, wherein said replication-defective ICP8/UL5-defective herpesvirus double mutant is a replication-defective ΔICP8/ΔUL5 HSV-2 strain.

3. The method of claim 2, wherein said cell line is a UL5/ICP8 expressing cell line.

4. The method of claim 3, wherein said cell line is a Vero cell line.

5. The method of claim 4, wherein said cell line exhibits the expression characteristics of cell line V295 as deposited with the ATCC and assigned deposit designation PTA-2403.

6. A method for producing an HSV-2 vaccine comprising the method of claim 5, and further comprising the step: (c) preparing a vaccine from the harvested virus of step (b).

7. A complementing cell line, wherein said cell line is able to support the propagation of a replication-defective, ICP8/UL5-defective HSV double mutant.

8. The cell line of claim 7, wherein said replication-defective, ICP8/UL5-defective HSV double mutant is an ICP8/UL5-defective HSV-2 strain.

9. The cell line of claim 8, wherein said ICP8/UL5-defective HSV-2 strain is a ΔICP8/ΔUL5 HSV-2 strain.

10. The cell line of claim 8, wherein said cell line is a UL5/ICP8 expressing cell line.

11. The cell line of claims 10, wherein said cell line exhibits the expression characteristics of cell line V295 as deposited with the ATCC and assigned deposit designation PTA-2403.

12. The cell line of claim 10 containing an ICP8/UL5-defective HSV-2 strain.

13. The cell line of claim 11 containing an ICP8/UL5-defective HSV-2 strain.

* * * * *